Figure 1:
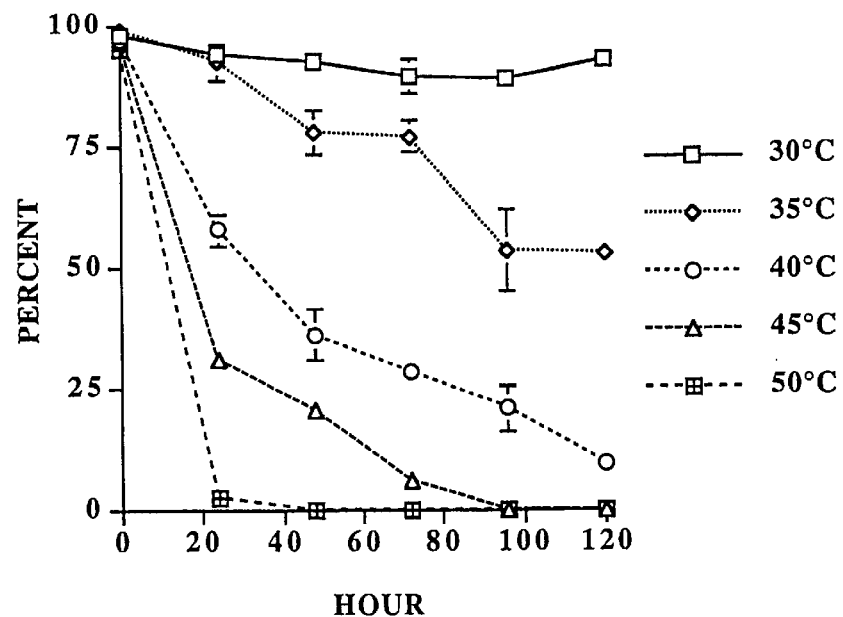

US006146843A

United States Patent [19]
Bowman et al.

[11] Patent Number: 6,146,843
[45] Date of Patent: Nov. 14, 2000

[54] METHOD AND APPARATUS FOR THE USE OF SENTINEL MICROORGANISM

[75] Inventors: Dwight D. Bowman; William C. Ghiorse, both of Ithaca; Michael B. Jenkins, Wellsville; Timothy Miller, Ithaca, all of N.Y.

[73] Assignee: Cornell Research Foundation, Inc., Ithaca, N.Y.

[21] Appl. No.: 09/386,736

[22] Filed: Aug. 31, 1999

Related U.S. Application Data
[60] Provisional application No. 60/098,498, Aug. 31, 1998.

[51] Int. Cl.[7] .............................. C12Q 1/24; C12Q 1/02; C12Q 1/22; C12Q 1/04
[52] U.S. Cl. .................. 435/29; 435/30; 435/31; 435/34; 435/255.3; 435/283.1; 435/285.1; 435/968
[58] Field of Search ................... 435/29, 30, 31, 435/34, 255.3, 283.1, 285.1, 968

[56] References Cited

PUBLICATIONS

Jenkins et al; Applied & Envir. Microb.; V65; p1998–2005 (May 1999).

Anguish, L. J. and W. C. Ghiorse. 1997. Computer–assisted laser scanning and video microscopy for analysis of *Cryptosporidium parvum* oocysts in soil, sediment, and feces. Appl. Environ. Microbiol. 63:724–733.

Blewett, D. A. 1989. Quantitative techniques in *Cryptosporidium* research, pp. 85–95. In: Angus, K. W. and D. A. Blewett (eds.), Cryptosporidiosis. Proceedings of the First International Workshop. The Animal Diseases Research Association, Edinburgh, UK.

Buijsman, E., H. F. M. Maas, and W. A. H. Aasman, 1987. Anthropogenic $NH_3$ emissions in Europe. Atmospheric Environ. 21:1009–1022.

Campbell, A. T., L. J. Robertson, and H. V. Smith. 1992. Viability of *Cryptosporidium parvum* oocysts: correlation in vitro excystation with inclusion or exclusion of fluorogenic vital dyes. Appl. Environ. Microbiol. 58:3488–3493.

Current, W. L. and L. S. Garcia. 1991. Crytosporidiosis. Clin. Microbiol. Rev. 4:325–258.

Dewes, T. 1996. Effect of pH, temperature, amount of litter and storage density of ammonia emmissions from stable manure. J. Agric. Res. 127:501–509.

Fayer, R. 1994. Effect of high temperature on infectivity of *Cryptosporidium parvum* oocysts in water. Appl. Environ. Microbiol. 60:2732–2735.

Fayer, R. and R. G. Leek. 1984. The Effects of reducing conditions, medium, pH, temperature, and time on in vitro excystation of *Cryptosporidium*. J. Protozool. 31:567–569.

Fayer, R. and T. Nerad. 1996. Effect of low temperatures on viability of *Cryptosporidium parvum* oocyst. Appl. Environ. Microbiol. 62:1431–1433.

(List continued on next page.)

*Primary Examiner*—Louise N. Leary
*Attorney, Agent, or Firm*—Brown, Pinnisi & Michaels, PC

[57] ABSTRACT

A sentinel chamber for containing microorganisms in a matrix, and methods for the use of the chamber in studying organisms in the field. The matrix is typically the same material as that within which the chamber will be placed. The chamber is made of a cylindrical body having a porous filter at each end. The filter at one end is contained under a snap-on cap, making the filling of the chamber quick and easy. The method of the invention uses the sentinel chambers to study the characteristics and survival of a sentinel organism in a particular environment. The medium present in the environment (i.e. soil, manure, sewage sludge, etc.) is placed in the sentinel chamber and a quantity of the sentinel organism (i.e. *C. parvum* oocysts) is injected into the medium. A filter is placed across the open end of the chamber, and held in place by the cap. The sentinel chamber is then buried or immersed in the environment (i.e. a field, manure pile, septic tank). After a specified time, during which the conditions in the environment are monitored, the sentinel chamber is removed and the organism studied.

34 Claims, 10 Drawing Sheets

OTHER PUBLICATIONS

Hillel, D. 1971. Soil and water. Academic Press, New York, NY. pp. 65–68.

Jenkins, M. B., L. J. Anguish, D. D. Bowman, M. J. Walker, and W. C. Ghiorse. 1997. Assessmen of a dye permeability assay for determination fo inactivation rates of *Cryptosporidium parvum* oocysts. Appl. Environ. Microbiol. 63:3844–3850.

Jenkins, M. B., D. D. Bowman, and W. C. Ghiorse. 1998. Inactivation of *Cryptosporidium parvum* oocysts by ammonia. Appl. Environ. Microbiol. 64:784–788.

Kirchmann, H., and E. Witter. 1989. Ammonia volatilization during aerobic and anaerobic manure decomposition. Plant Soil. 115:35–41.

MacKenzie, W. R., N. J. Hoxie, M. E. Proctor, S. Gradus, K. A. Blair, D. E. Peterson. JT Kazmierczak, K. Fox, D. G. Addis, J. B. Rose, and JT Davis. 1994. Massive waterborne outbreak of *Cryptosporidium* infection associated with a filtered public water supply, Milwaukee, Mar. and Apr., 1993. New England J. Med. 331:161–167.

Madore, M. S., J. B. Rose, C. P. Gerba, M. J. Arrowood, and C. R. Sterling. 1987. Occurrence of *Cryptosporidium* oocysts in sewage effulents and selected surface waters. J. Parasitol. 73:702–705.

Moore, A. C., B. L. Herwaldt, G. F. Craun, R. L. Calderon, A. K. Highsmith, and D. D. Juranek. 1994. Waterborne disease in the United States, 1991–1992. J. Am. Water Works Assoc. 86(2):87–99.

Pavelic, P., et. al., Diffusion Chamber Method For In Situ Measurement Of Pathogen Inactivation In Groundwater, Water Resources 32(4), p. 1144 (1998).

Peng, M. M., L. Xiao, A. R. Freeman, MT Arrowood, A. A. Escalante, A. C. Weltman, C. S. L. Ong, W. R. MacKenzie, A. A. Lal, and C. B. Beard. Genetic polymorphisms among *Cryptosporidium parvum* isolates: evidence of two distinct human transmission cycles. Emerging Infectious Diseases 3:567–573.

Roberson L. J., A. T. Campbell, and H. V. Smith. 1992. Survival of *Cryptosporidium parvum* oocysts under various environmental pressures. Appl. Environ. Microbiol. 58:3494–3500.

Roberson, L. J., A. T. Campbell, and FIN. Smith. 1993. A low cost, low technology container for studying the survival of transmission stages of parasites and other pathogens in water–related environments. Wat. Res. 27:723–725.

Rose, J. B. 1988. Occurrence and significance of *Cryptosporidium* in water. J. Am. Water Works Assoc. 80:53–58.

Rose, J. B., A. Cifrino, M. S. Madore, C. P. Gerba, C. R. Sterling, and M. J. Arrowood. 1986. Detection of *Cryptosporidium* from wastewater and freshwater environments. Water Sci. Technol. 18;233–239.

Topp, G. C. 197 1. Soil water hysteresis in silt loam and clay loam soils. Wat. Resources Res. 7:914–920.

Walker, M. J., C. Montemagno, J. C. Bryant, and W. C. Ghiorse. 1998. Method detection limits of PCR and immunofluorescence assay for *Cryptosporidium parvum* in soil. Appl. Environ. Microbiol. 64:2281–2283.

Weatherburn, M. W. 1967. Phenol–hypochlorite reaction for determination of ammonia. Anal. Chem. 39:971–974.

Watershed Agricultural Progarm Progress Report, 1997, "Pollution Prevention Through Agricultural Management", 3 pages.

Watershed Agricultural News, Dec. 1996, "Farm Profile: Wild Flower Farm", 2 pages.

the advantage of using an inert polycarbonate
METHOD AND APPARATUS FOR THE USE OF SENTINEL MICROORGANISM

REFERENCE TO PROVISIONAL APPLICATION

This application claims an invention which was disclosed in Provisional Application No. 60/098,498, filed Aug. 31, 1998, entitled "METHODS AND APPARATUS FOR THE USE OF SENTINEL MICROORGANISMS". The benefit under 35 USC §119(e) of the United States provisional application is hereby claimed, and the aforementioned application is hereby incorporated herein by reference.

FIELD OF THE INVENTION

The invention pertains to the field of microbiological methods and apparatus. More particularly, the invention pertains to a chamber for the use of a sentinel organism in field or laboratory studies, and the use of the chamber in such studies.

BACKGROUND OF THE INVENTION

The following discussion is extracted from "DIFFUSION CHAMBER METHOD FOR IN SITU MEASUREMENT OF PATHOGEN INACTIVATION IN GROUNDWATER", Paul Pavelic, et. al, *Water Resources* 32(4), pg. 1144 (1998):

"An understanding of the survival of pathogenic organisms (through the use of indicator or enteric species) is used to minimize the risk of infection. Clearly, the longer a pathogen survives in the environment, the greater the probability of transmitting infection. Transmission of infection by pathogens present in abstracted groundwaters was one of the earliest recognized public health problems—that of cholera, discovered by John Snow at the Broad St. pump in London.

"The subsurface environment is one which tends not to favor the survival of introduced microorganisms. Survival (and transport) of pathogenic microorganisms depends on the nature of the porous media, environmental conditions, and the type of microorganism. . . . A number of techniques have been used to measure pathogen inactivation in groundwater, although each of these have particular advantages and disadvantages. Laboratory batch experiments are simple and the most commonly used. However the extent to which these replicate the subsurface conditions is questionable, because of, for example, the lower hydrostatic pressure and redox effects (exposure to $O_2$) that are associated with their use in the laboratory. That is, processes governing survival may differ between the laboratory and the field. Therefore, availability of techniques to measure rates of pathogen inactivation in situ is an attractive development.

"Field isolation methods, where organisms are introduced directly into the groundwater, have been attempted, but can be extremely difficult to interpret due to mixing between introduced and ambient waters within the aquifer, the differential residence times of abstracted waters, and the impact of indigenous organisms. There are also public health considerations in relation to uncontrolled release of pathogens into the environment.

"The containment of well-defined suspensions of microorganisms within dialysis tubing is a relatively simple and inexpensive approach to determine in situ inactivation rates. However dialysis tubing is composed of cellulose, which can be catabolised by bacteria, making it fragile and so subject to tearing. Hence it may not be a reliable experimental technique to use under field conditions.

"Use of diffusion chambers for studying microbial survival was first reported by McFeters and Stuart, (1972), and applied to studies of natural surface waters. Diffusion chambers are similar to dialysis tubing, but have the advantage of using an inert polycarbonate membrane, which allows diffusive flow across the chamber membrane. Other workers who have reported use of diffusion chambers in groundwater studies are: McFeters et al. (1974) for indicator bacteria and Keswick et al. (1982) for enteric viruses and indicator bacteria. In both cases, the chambers were placed in tanks where groundwater flowed past them while being pumped continuously from a well. The high flow of water past the chambers was not representative of groundwater conditions, whilst the tank overflow provides a large artifact.

"Since each chamber required individual housing, there was considerable effort and much replication, in chamber construction and preparation. And since the dimensions were also reduced to fit in small diameter wells, the Plexiglas bodies of the chambers became fragile, and thus susceptible to damage. . . . Several means of sterilizing the plexiglass chambers were tested or explored, autoclaving, chemical disinfection, microwave and radiation, and difficulty was found with each. For instance, attempts to autoclave the Plexiglas chambers resulted in their deformation, which also made them prone to leakage."

Pavelic proposed a diffusion chamber consisting of a frame and detachable matching side-pieces that are constructed from nylon. Holes were bored into this frame. and two filter membranes attached by side-pieces to create the surface area of the chamber. Polycarbonate membrane filters of 0.025 um pore-size (Millipore Type VS) with nylon mesh reinforcing on the outer surface are trimmed to size and sandwiched firmly between the side pieces and main frame by stainless steel screws. Two holes were drilled into one side of the chamber to allow catheter single lumen PVC tubing (0.59 mm ID) for injecting sampling and re-injecting the fluid from the chamber using a syringe. Excess catheter tubing was fed into a hole drilled into the frame. Liquid flowing silicon glue also provided watertight seals along all joints. The Pavelic chambers were thus expensive, time-consuming and complicated to build and use—"we anticipate that seven person-hours of work, spread over two days, is required per assembly" (of nine chambers).

Kennedy, U.S. Pat. No. 3,787,183, "METHOD OF ANALYZING CATALYST ACTION", presents a method of analyzing a catalyst by burying samples of a catalyst in durable perforate containers at known locations in a larger body of catalyst. No use of sentinel organisms is shown, and the method is intended to study the catalyst itself, not the effect of the catalyst (environment) on organisms. The perforate containers are of different structure from the sentinel chambers of the invention.

Michaels, et al, U.S. Pat. No. 4,440,853, "MICROBIOLOGICAL METHODS USING HOLLOW FIBER MEMBRANE REACTOR", teaches the use of microorganisms for processing organic material, where the organisms are suspended in a spongelike structure surrounding a semipermeable membrane.

Cullimore, et al, U.S. Pat. No. 5,187,072, "METHOD AND APPARATUS FOR THE DETERMINATION OF FERMENTATIVE ANALYTIC CULTURED ACTIVITIES", uses an inverted test chamber in a medium to study an organism. The production of gas by the organism causes the chamber to float.

Nolte, et al, U.S. Pat. No. 5,307,694, "SAMPLE HOLDER FOR HYDROUS PYROLYSIS OPERATIONS", shows the use of a similar sample chamber to the invention, in that the sample chamber comprises a cylindrical tube with filters at each end, within which a sample is placed. However, no medium or sentinel microorganism is used, and the use of the chamber is quite different, involving solvents and vacuum analysis and high temperatures to extract hydrocarbons.

Machelsky, et al, U.S. Pat. No. 5,516,648, "ENCAPSULATED BIOLOGICAL INDICATOR", encapsulates reference microorganisms in an interior cavity of a microporous membrane, rather than a sentinel chamber.

Hollingshead, U.S. Pat. No. 5,698,413, "METHOD OF EVALUATING CHEMOTHERAPEUTIC AGENTS IN VIVO", implants semipermeable encapsulation devices containing target cell lines into laboratory animals for studying the effect of chemotherapy on the cell lines.

SUMMARY OF THE INVENTION

The invention presents a simple, easy to use sentinel chamber for containing microorganisms in a matrix, and methods for the use of the chamber in studying organisms in the field. The matrix is typically the same material as that within which the chamber will be placed. The chamber is made of a cylindrical body having a porous filter at each end. The filter at one end is contained under a snap-on cap, making the filling of the chamber quick and easy.

The method of the invention uses the sentinel chambers to study the characteristics and survival of a sentinel organism in a particular environment. The medium present in the environment (i.e. soil, manure, sewage sludge, etc.) is placed in the sentinel chamber and a quantity of the sentinel organism (i.e. *C. parvum* oocysts) is injected into the medium. A filter is placed across the open end of the chamber, and held in place by the cap. The sentinel chamber is then buried or immersed in the environment (i.e. a field, manure pile, septic tank). After a specified time, during which the conditions in the environment are monitored, the sentinel chamber is removed and the organism studied.

BRIEF DESCRIPTION OF THE DRAWING

FIG. 1. Effect of temperature on oocyst viability as determined by the dye permeability assay. Each datum point represents the mean percentage±the SE for at least duplicate samples in which 100 oocysts were characterized at random. SE bars that are not visible are smaller than the symbols in the graph.

FIG. 2. Effects of soil water potential at a constant temperature of 25° C. on oocyst viability as determined by the dye permeability assay. Each datum point represents the mean percentage±the SE for at least duplicate samples in which 100 oocysts were characterized at random. SE bars that are not visible are smaller than the symbols in the graph.

FIG. 3.A. Viability of sentinel and control oocysts that were exposed to the interior environment of the first calf manure pile (November 1996 to May 1997). Viability of oocysts was determined by the dye permeability assay. Each datum point represents the mean±SE of 3 replicate and 2 subsamples of each replicate for a total of 6 subsamples with 100 oocysts characterized at random per subsample.

FIG. 3.B. Average daily temperature of the interior of the manure pile where sentinels and controls were situated.

FIG. 4.A. Viability of sentinel and control oocysts that were exposed to the interior environment of the second calf manure pile (January 1998 to June 1998). Viability of oocysts was determined by the dye permeability assay. Each datum point represents the mean±SE of 3 replicate and 2 subsamples of each replicate for a total of 6 subsamples with 100 oocysts characterized at random per subsample.

FIG. 4.B. Average daily temperature of the interior of the manure pile where sentinels and controls were situated.

FIG. 5. Results of the dye permeability assay on sentinel and control oocysts from the second calf manure pile.

FIG. 6.A. Viability of sentinel and control oocysts that were exposed to a surface soil environment from November 1996 to March 1997. Viability of oocysts was determined by the dye permeability assay. Each datum point represents the mean±SE of 3 replicate and 2 subsamples of each replicate for a total of 6 subsamples with 100 oocysts characterized at random per subsample.

FIG. 6.B. Average daily temperature of the interior of the manure pile where sentinels and controls were situated.

FIG. 7.A. Viability of sentinel and control Oocysts that were exposed to a surface soil environment from January 1998 to May 1998. Viability of oocysts was determined by the dye permeability assay. Each datum point represents the mean±SE of 3 replicate and 2 subsamples of each replicate for a total of 6 subsamples with 100 oocysts characterized at random per subsample.

FIG. 7.B. Average daily temperature of the interior of the manure pile where sentinels and controls were situated.

FIG. 8. Results of the dye permeability assay on sentinel and control oocysts from the first surface soil environment.

FIG. 9. Results of the dye permeability assay on sentinel and control oocysts from the second surface soil environment.

FIG. 10 is a cross-sectional view of a sentinel chamber of the invention.

FIG. 11 is a view of a sentinel chamber of the invention, with a penny for scale.

FIG. 12 is a flowchart of the method of the invention

DETAILED DESCRIPTION

Apparatus

The apparatus of the inventions is a "sentinel chamber", intended to contain a microorganism which an experimenter wishes to study in its environment, without the likelihood that the sentinel organism will escape or external organisms contaminate the chamber. FIGS. 10 and 11 show the sentinel chamber of the invention.

The chamber is made up of a body enclosing an interior volume, such as a cylindrical microcentrifuge tube (3). One end of the tube (3) has a filter (4), permitting infiltration of gas or liquid, but preventing the contents of the tube from leaving.

The tube (3) is filled with a material (5), which is the same as the environmental material within which the sentinel chamber is to be located, such as manure, sand, earth, sewage sludge, or the like. The open end of the tube is closed by a cap (1), which has a hole (7) centrally located. A filter material (2) is placed under the cap (1), so that liquids and gasses may infiltrate through into the chamber, but the contents may not escape. The filter material may be a mesh, such as the nylon mesh used in the examples below, or a sintered metal material such as sintered stainless steel, or any other porous material. The pores in the porous material must be of such a size as to retain the sentinel organism in the chamber, but allow the free passage of fluids.

Alternatively, the chamber could be in some other shape, such as a disk or cube or dodecahedron, or some other shape, in which an area is covered with, or made of, a filter material. If desired, the entire body could be made of a porous material.

A sentinel microorganism is introduced into the sentinel chamber, either by being pre-loaded with the material, or by being injected through the filter mesh by a needle. The examples below use the microorganism *Cryptosporidium parvum*, but it will be understood that other organisms, such as *Ascaris suum* eggs, or *Giardia lamblia* cysts may be used as required.

In the experimental work detailed below, the sentinel chamber was made from a commercially produced basket of a microfiltration system (Osmonics, Livermore, Calif.) with a nylon 0.45 um filter built into one end was the principal component of the sentinel container. On the open end, either a 10- or 60 um nylon mesh filter (Spectramesh™, Markson, Inc., Hillsboro, Oreg.) was secured with the cap of the microcentrifuge tube that was cut free from the microcentrifuge and a hole punched through it with a #4 cork borer.

Figure 11:

The picture of FIG. 11 shows the sentinel chamber as used in the examples, with a penny for scale. The chamber as shown was approximately 2.5 cm tall and 0.8 cm in diameter, although it will be understood that various sizes of chambers may be used within the teachings of the invention. Similarly, the mesh sizes of the filter may vary, so long as the filter pores are small enough that neither the sentinel organism nor the medium may escape, and the pores are large enough to permit the free flow of environmental gasses and liquids, so that the sentinel chamber can quickly equilibrate to the environment.

The sentinel chambers of the invention could be commercially pre-loaded with a chosen sentinel organism in a liquid medium (possibly with particulate matter), and shipped to researchers for use in the field. The medium, as well, could be selected from a number of standard or specialized media of interest to researchers.

If the sentinel chambers are to be used in a liquid or semi-liquid environment, they will need to be weighted, and potentially could be lost under field conditions. If desired, a magnetic metal ring (6) could be attached to, or embedded in, the cap (1) or tube (3). This will allow recovery of the chamber by magnets or detection by metal detectors, and selection of the size and material of the metal ring will allow adjustment of the buoyancy of the chamber.

The sentinel organisms can be made to fluoresce, if desired, either by incorporating a fluorescent stain into the organism or by incorporating the gene for fluorescent protein into the organism.

Method

Figure 12:
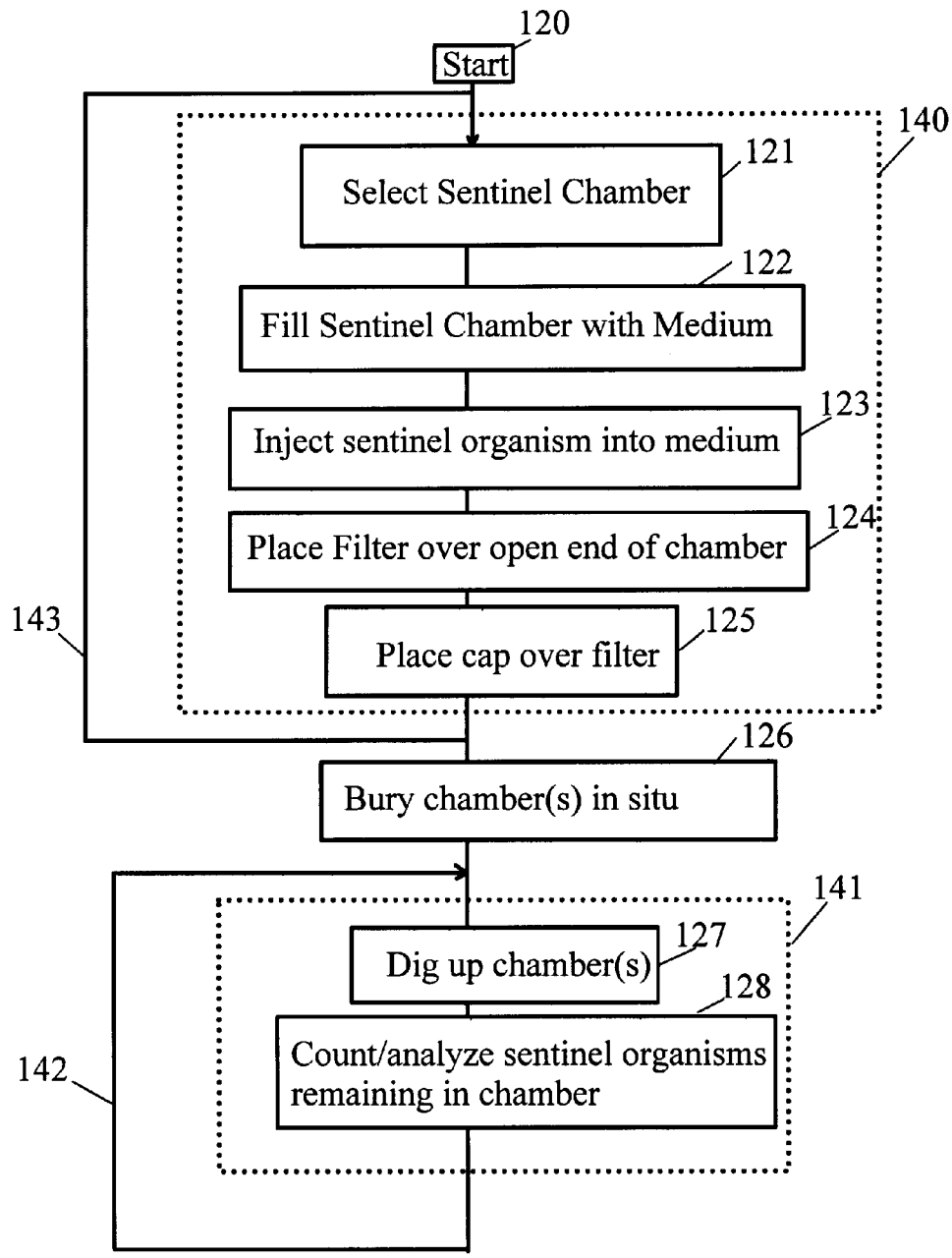

The method of the invention, as charted in FIG. 12, uses the sentinel chambers to study the characteristics and survival of a sentinel organism in a particular environment.

The first step of the method (140) is to prepare a number of sentinel chambers. A sentinel chamber is selected (121) and the medium present in the environment (i.e. soil, manure, sewage sludge, etc.) is placed in the sentinel chamber (122). The medium may be sterilized, by conventional methods, to ensure that only the introduced sentinel organism is present in the medium. If needed, the medium may be hydrated by the addition of water, preferably distilled water so as not to introduce unwanted chemicals or organisms.

A quantity of a sentinel organism (i.e. *C. parvum* oocysts, *Ascaris suum* eggs, *Giardia lamblia* cysts, or other organisms as selected for the application) is injected into the medium (123). This quantity will vary depending on the organism and the experimental design. If desired, several different organisms could be introduced.

A filter is placed across the open end of the chamber (124), and held in place by the cap (125). This step is repeated (143) until a sufficient quantity of sentinel chambers have been prepared. As noted above, this step could be performed commercially, and pre-loaded chambers supplied by a supplier to experimenters.

It is also possible to inject the organism into the sentinel chamber by pushing a syringe through the filter material, if for some reason it is desirable to prepare and close the sentinel chamber first. In such a case, step (123) would be done after steps (124) and (125).

The sentinel chamber is then buried or immersed in the environment (i.e. a field, manure pile, septic tank) (126). The chambers may be placed in groups at differing locations or depths, or all together, depending on the design of the experiment. Monitoring equipment may be buried with or around the chambers for taking measurements of the environment during the experimental period.

After a specified time, during which the conditions in the environment are monitored (141), one or more of the sentinel chambers is removed (127) and the organism studied (128). These last steps may be repeated (142) so as to ascertain the characteristics of the organism in its environment over time, or all of the chambers at differing locations may be removed at once to ascertain the relationship of various spatial characteristics to the organism. An experimenter skilled in the art would recognize other variations and applications of the sentinel chambers to various experimental designs.

METHOD EXAMPLE 1

Use of Sentinel *Cryptosporidium parvum* Oocysts for Field Measurements of Oocyst Inactivation Abstract Freshly prepared sucrose-purified *Cryptosporidium parvum* oocysts were used as sentinels to measure their survival kinetics in passive manure piles and the surface soil of a field where manure spreading occurred. The sentinel oocysts were contained in the basket of a sentinel chamber filled with air-dried and sieved (2 mm) calf manure or soil. The chamber was made of a modified microcentrifuge basket. At one end of the basket was a fixed 0.45 um filter; at the open end a 60 um mesh filter was secured by the microcentrifuge cap into which a hole had been cut.

The air-dried field manure and soil were brought to near water holding capacity by allowing the material to wick up water from a reservoir, and then brought to near saturation by inoculating with 2 million oocysts in an aqueous suspension. The sentinel containers had been tested for their ability to equilibrate with solutes and water potential of the external environment.

The inoculated sentinel containers and controls (purified oocysts in either PBS or distilled water contained in sealed microcentrifuge tubes) were buried in the interior of 2 passive manure piles along with two data loggers to record the internal temperature of the manure where the sentinel containers and controls were located. Sentinel containers inoculated with purified oocysts and controls were placed 3 cm into the surface of a field soil along with two data loggers for recording soil temperature. Sentinel containers and controls were removed every two to four weeks after establishment.

Oocysts were extracted by a cold sucrose floatation procedure, and viability was determined by a dye permeability assay. Viability of the sentinel oocysts in the manure pile decreased significantly more rapidly than their counterpart controls indicating that factors (other than temperature) associated with exposure to the manure enhanced oocyst inactivation.

In the first (1996–1997) surface soil field experiment sentinel oocysts and controls remained equal and constant for several weeks when the soil temperature was steady around 5° C.±2° C. After several days of freeze-thaw cycles, however, the sentinel oocysts were more than 99% nonviable; whereas, controls were never reduced to less than 50% nonviable, indicating that exposure to the soil itself was a factor in oocyst inactivation.

A similar pattern was observed in a second field experiment at the same site although the rate of inactivation was not as great as the previous year and appeared to be correlated with the number of freeze-thaw cycles, or the difference between an El Niño and non-El Niño year. To relate the effects of composting temperatures that may occur in a passive manure pile, laboratory experiments testing oocyst survival at temperatures between 30° and 50° C. were undertaken. The effects of various soil water on oocyst survival were also tested in the laboratory.

Introduction

Because of several large-scale outbreaks of cryptosporidiosis attributable to contaminated public water systems (MacKenzie et al., 1994; Moore et al., 1994) concern about *Cryptosporidium parvum* oocysts, the transmissive agent, has gained official recognition as seen in the enactment by the USEPA of the Information Collection Rule (ICR). There are two main sources of infectious oocysts in surface waters of watersheds providing drinking water to urban populations, sewage treatment plants (Madore et al., 1987; Bukhari et al 1997), and non-point sources such as dairy farms (Rose, 1988). Neonatal calves are prone to cryptosporidiosis, and can shed billions of oocysts over the duration of their infection (Blewett 1989). It is well established that cryptosporidiosis is zoonotic (Current and Garcia, 1991), although genetic distinctions between human and bovine isolates of *C. parvum* have been reported (Peng et al., 1997).

In some watersheds across the country where dairy farming is relatively intense, efforts to manage potential sources of *C. parvum* oocysts have increased. Although there are now a number of published reports on environmental parameters affecting the survival of oocysts such as temperature extremes, pH extremes, exposure to ammonia, and desiccation (Fayer, 1994; Fayer and Nerad, 1996; Robertson et al., 1992; Jenkins et al., 1997; Jenkins et al. 1998), there is essentially no data indicating the survival dynamics of oocysts under field conditions.

The method and apparatus of the invention will allow questions regarding farm management practices to be answered, such as: Will passive composting of calf manure accelerate oocyst inactivation? How does spreading manure containing oocysts on fields (a common practice) affect oocyst inactivation?

Using a container for measuring the effects of water-related environments on the survival of oocysts (Robertson et al, 1993), Robertson et al. (1992) reported on the effects of tap water and river water on *C. parvum* oocysts. In an analogous fashion we have designed a sentinel container that will allow the oocysts to be in a porous medium like calf manure and soil. In this sentinel chamber equilibrium between the contents of the container and the exterior environment can be reached, and the oocysts can over time be extracted and tested for viability. There were two main objectives of this investigation:

1) to test the sentinel chambers under field conditions, and
2) to use the data from the test to estimate the efficacy of passive composting of calf manure, and spreading of calf manure in the field on the inactivation of *C. parvum* oocysts.

Materials and Methods

Oocyst Purification.

Feces from 6- to 20-day-old Holstein calves with cryptosporidiosis were processed using a continuous-flow differential density flotation method previously described (Jenkins et al., 1997). Purified oocysts were washed by centrifugation 3 times in cold distilled water at 2100×g for 10 min. to remove sucrose, adjusted to a concentration of $10^7$ ml$^{-1}$ and stored in distilled water containing 100 units of penicillin G sodium ml$^{-1}$, 100 ug streptomycin sulfate ml$^{-1}$, and 0.25 ug amphotericin B ml$^{-1}$ of suspension at 4° C. Each lot of purified oocysts was tested by the dye-permeability assay (see below) after purification, and periodically during storage. Some lots were also tested with the in vitro excystation assay (see below).

Dye-permeability Assay.

The details of this assay have been described (Anguish and Ghiorse, 1997; Jenkins et al, 1997). Stock solutions of 4'-6-diamidino-2-phenylindole (DAPI) (2 mg ml$^{-1}$ in HPLC grade methanol) and propidium iodide (PI) (1 mg ml$^{-1}$ in 0.1 M PBS: 0.028 M $NaH_2PO_4.H_2$ 0,0.072 M $Na_2HPO_4$, 0.145 M NaCl, pH 7.2) were added to aliquots, of the sample in a 1.5-ml microcentrifuge tube at a ratio of 1 to 10 (v:v), the contents of the tube were mixed with a Vortex™, and the tubes were incubated in the dark at 37° C. for 2 h. Each aliquot was stained with Hydrofluor antibody (Meridian Diagnostics, Cincinnati, Ohio or EnSys Environmental Products, Inc., Research Triangle Park, N.C.) as described (1), washed twice with PBS and resuspended to their original volume in 0.3 M 1,4-diazabi-cyclo [2,2,2] octane (DABCO) in 0.1 M PBS (pH 7.2) (DABCO/PBS). The samples were stored in the dark at 4° C. until examined (within 72 h) using the microscope and microscopic procedures as described (1, see below).

Laboratory Tests of Sentinel Chamber.

Containment determinations: A 100 ul aliquot of purified oocysts ($10^7$ oocysts ml$^{-1}$) was pipetted into each of ten microfiltration baskets. The baskets were placed in their complementary microcentrifuge tubes, and centrifuged at 200×g for 3 min.; thus all liquid was out of the basket and in the microcentrifuge tuber. A 15 ul aliquot of a 1% solution of Noble Agar (Difco) was added to each filtrate, and mixed on a Vortex mixer. Two 50 ul aliquots from each of the ten filtrate-Noble Agar mixes were then placed in wells of a microscope slide, stained with the Hydrofluor antibody stain according to the manufacturer's instructions, and observed microscopically.

Two experiments were designed to test the ability of the 0.45 um nylon filter to allow equilibration to occur between internal and external environments:

1) Knowing that ammonia will inactivate oocysts as determined by both the dye permeability assay and in vitro excystation (Jenkins et al, 1998) an aqueous suspension of freshly purified and viable oocysts were placed in microfiltration baskets, sealed with caps that were removed from their complementary microcentrifuge tubes, and in duplicate, were immersed in a Parsons Ammonia solution and in distilled water as a control. Baskets were removed after 24 h, the oocysts removed from the baskets, and stained for viability by the dye permeability assay.

2) Oven-dried and sieved (1 mm) soil was added to a stainless steel pan (18×30 cm) to a depth of 5 cm. the soil was then saturated with distilled water and allowed to equilibrate for one day at room temperature (24±1° C.). The sentinel chambers were tared before they were filled with the dried, sieved soil. The filled sentinel chambers were then placed, 0.45 um filter down, in a reservoir of distilled water to allow water to wick up the soil column inside the chamber. The chambers were kept in the reservoir of water for 24 h to allow them to reach a state of water holding capacity after which they were weighed. The chambers were then placed, 0.45 um filter down, in the wetted soil. In triplicate, sentinel chambers were randomly removed, as well as samples from the bulk wetted soil; water content was determined by drying the soil samples at 105° C. for 12 h, and using the gravimetric water content formula, (sample wt—oven-dried wt)/oven-dried wt. Gravimetric water contents were taken at time 0 and approximately every 24 h. The bulk soil was rewetted with 200 ml distilled water at 49.5, 146.5 and 243.5 h. The test was terminated after 333.5 h.

In addition to the laboratory tests of the chamber's ability to equilibrate with the external environment, soil gravimetric water content of the soil inside the chambers (with a 60 um mesh filter secured at one end to the chamber as described above) was compared to the gravimetric water content of the bulk field soil in which they were buried.

Temperature Experiments.

Because temperatures between ambient and 55° C. can be reached on composting material, purified oocysts ($10^6$ 100 $ul$) suspended in PBS were incubated at 30, 35, 40, 45, and 50° C. for 5 days. Duplicate samples were removed every 24 h, and assayed for viability by the dye permeability assay. Two 10 ul subsamples of each tube were examined. At least 100 oocysts per subsample for a total of 400 oocysts were visually characterized per sample.

Soil Water Potential Experiments.

Because the effects of soil water potential on the survival of oocysts is not known (to the best of our knowledge), oocysts were inoculated into oven-dried (105° C.) and sieved (2 mm) surface (0 to 4 cm-depth) soil that was taken from the field site. A soil moisture relief curve (soil gravimetric water content versus soil water potential) for this soil was established by the Soil Testing Lab of the Department of Soils, Crops, and Atmospheric Sciences at Cornell University. Gravimetric water contents were determined for soils at 0.33, 1, 3, 5, 10, and 15-bars as determined by a pressure plate. Regressing % soil water content against the natural log (ln) of the pressure plate measurements (using Cricket Graph III for Macintosh [Computer Associates International, Inc., Islandia, N.Y.]) yielded a linear equation with $r^2=0.962$, $y=-5.028x+26.002$ where y=% soil moisture and x=ln(pressure plate measurement). Five % soil water contents representing the soil's approximate field capacity (FC), or water holding capacity, and 80, 60, 40, and 20% FC were used; these were, including their respective water potential values, 43.1% (403 bars), 34.5% (418 bars), 25.9% (−1.0 bars), 17.2% (−5.8 bars), and 8.6% (−31 bars). Differences in soil water potential attributable to hysteresis is assumed to be negligible based on previous studies: Hillel (1971) stated that "the hysteresis effect is in general more pronounced in coarse textured soils in the low suction range, where pores may empty at a much larger suction than that at which they fill." The main point is that the phenomenon of hysteresis occurs mainly at "the low-suction range." This is confirmed by data reported by Topp (1971) in which it is shown that a clay loam soil hysteresis occurs in the suction range of 0 to −0.34 bars, and for a silt loam soil hysteresis occurs between 0 and −0.42 bars. After equilibration of the rewetted soils there should be negligible hysteresis effect for the soils calibrated to <−1 bar. Into tared microcentrifuge tubes, approximately 1 g oven dried and sieved (2 mm) soil was added to the microcentrifuge tubes. Calculated quantities of distilled water pipetted into the soil and the microcentrifuge tubes sealed and allowed to equilibrate before being inoculated with oocysts. The full quantity of water added was lacking 25 ul aliquots of inoculant which were added after the added water was allowed to equilibrate with the soil at room temperature, 24±1° C. The 25 ul of inoculant contained $2\times10^6$ oocysts. After inoculation the tubes were sealed and incubated in the dark at 4° C. for 48 h, and at 25° C. for 20 days. At day 2, 4, 10, and 20 duplicate tubes incubating at 25° C. and representing each soil water potential were sampled. Sampling consisted of extracting oocysts from the soil as described below, and examined for viability by the dye permeability assay.

Sentinel Preparation and Oocyst Extraction.

Sentinels were filled with airdried and sieved (2 mm) calf manure (a grab sample from the passive manure pile where the study was established) or air-dried and sieved (2 mm) soil taken from the field in which the site was to be established (see below). Oocysts were not detected in the dried, sieved manure before inoculation. Before wetting and inoculating the sentinel containers, all containers were identified by number, tared, and weighed when filled and sealed with the Spectra Mesh filter; thus water content determinations could be made after removing the sentinel containers from their respective field sites. With the 0.45 um filter down, the filled sentinels were placed in a reservoir of distilled water as described above and allowed to reach a water content close to water holding capacity. A 100 ul aliquot of an aqueous suspension of freshly purified oocysts ($2\times10^7$ $ml^{-1}$) was injected into the wetted contents with a syringe.

For extracting the inoculated oocysts, a protocol described by Walker et al. (1998) was used. The 0.45 um filter was excised with a razor blade, the cap and Spectra Mesh were removed, and the whole container placed in a 50 ml centrifuge tube to which was added 10 ml of a 0.1% solution of Tween 80 in 1×PBS. The tubes were sealed and placed on a rotary shaker at 200 rpm for 20 min. After the empty containers were removed, the suspension of material was underlain with a cold (4° C.) sucrose (1.18 specific gravity) solution, and centrifuged at 1500×g for 20 min. The interface between sucrose and Tween 80 PBS was removed with a syringe (~10 ml), transferred to another 50 ml centrifuge tube, further diluted with PBS to 50 ml, and centrifuged at 1500×g for 30 min. The supernatant was aspirated off leaving 1 ml of supernatant above the pellet. The pellet was resuspended and transferred to a 1.5 ml microcentrifuge tube, and sedimented in a microcentrifuge at 11,300×g for 1 min., the supernatant discarded, the pellet resuspended in 100 ul PBS, and stained as described above for viability.

Efficiencies of extracting oocysts from the manure and soil samples were determined by counting extracted oocysts that had been stained with the Hydrofluor antibody. Counting was done with a Neubauer-Levy-Hausser counting chamber as previously described (Jenkins et al., 1997). Extraction efficiency on the manure was determined for four sentinel chambers removed from the first manure pile on the last day of sampling (day 145). Extraction efficiency on the soil was determined on two occasions: 1) on triplicate 1 g oven-dried and sieved soil samples maintained (by sealing in a 1.5 ml microcentrifuge tube) at a soil water potential of −0.33 bars (near field capacity) and incubated at 24±1° C. for 10 days; and 2) on 6 sentinel containers that had been removed from the field on day 175 and allowed to reach a soil water content that ranged from 4.2 to 7.9% (a soil water potential that ranged from −140 to <−800 bars).

Field Experiments

Sites of Passive Manure Pile:

Two dairy farms (both in Delaware County, N.Y.) on which our experimental sites were established had a designated place for the collection and piling of calf manure and bedding that was removed periodically from calf hutches, (in the first experiment), and barn facility (in the second experiment) housing neonatal calves. The first (1997) pile was protected by a roof and three walls; the second (1998) was open to the elements. A sample of this material was removed to the laboratory where it was air-dried and sieved (2 mm) in preparation for filling the sentinel containers.

On the day of establishing the experiment, the first pile had approximate dimensions of 4 m wide, 3 m deep, and 1.5 m high; the second pile had approximate dimensions of 3.5 to 4 m diameter, and 1.5 m deep. To be able to remove sentinels periodically from the piles whose size was to increase over the duration of the experiment, a set of replicate sentinels and controls were attached to fishing line, and placed in the trough that had been cut out at the end of 1.2 cm diameter PVC piping. This allowed the sentinels to be directly exposed to the surrounding manure material, and thus become equilibrated with the external environment, and also allow the researcher to remove the sentinels by pulling the piping out at time of sampling. From the top of the manure pile a hole in the middle of each pile was dug to place 10 sets of replicate sentinels and controls in the interior of the pile. Two HOBO Data Loggers (Onset Computer Corporation, Pocasset Mass.) were placed next to the sentinels and recorded the temperature of the pile over the duration of the experiment.

After the sentinels, controls, and data loggers were in place, they were covered with the manure and the hole filled in. The sentinels and controls were then left undisturbed except at times when the piping containing the sentinels and controls were removed by pulling the piping out of the pile with minimal disturbance to the pile. At time of sampling, a set of sentinels and controls were removed, placed on ice, and taken to the laboratory for extraction of oocysts, and analysis for viability. The first site was established late November 1996, and was terminated mid March 1997; the second site was established Jan. 15, 1998, and terminated May 7, 1998.

Ammonia Determination for Second Manure Pile:

Following a protocol adapted from Dewes (1996), two 14 cm petri plates secured to a wire test tube rack and containing in each 75 ml of a 0.02 M $H_3PO_4$ solution were placed on a leveled interior portion of the manure pile. It was covered with a plastic wash basin that was sealed around the petri plates. The phosphoric acid solution was allowed to trap gaseous ammonia for 6 hours. At the end of the incubation period, the phosphoric acid solution was pipetted into a brown bottle. Analysis of the ammonia trapping solution was undertaken following the protocol described by Weatherbum (1967). At the termination of the second experiment, when the data loggers were recovered, and the last set of sentinel containers and controls were removed, a grab sample of manure was taken from where the sentinel containers were located, put in a whirlpack and stored on ice. This sample was taken to the Cornell Nutrient Analysis Laboratory where it was analyzed to determine available $NH_3$ and pH in water. The sample was extracted with 2M KCl and analyzed by an automated phenate method.

Site of Surface Soil Experiment:

The site was on a field where manure spreading regularly occurred. The soil was a silt loam (described in Table 1). The first experiment was established Nov. 13, 1996, and ended Mar. 5, 1997; the second experiment was established near the first experiment on Jan. 13, 1998, and terminated May 7, 1998. Termination occurred in each case when the dairy farmer prepared the field for planting corn. Wetted and inoculated sentinel chambers were placed in a container of air-dried and sieved (2 mm) soil from the site that had been wetted to field capacity. Included with the sentinel chambers were microcentrifuge tubes containing a one ml suspension of $2\times10^6$ oocysts in PBS for the first experiment, and distilled water for the second experiment. The sentinel chambers and controls were thus transported on ice to the field site in Delaware Counter, N.Y. A shallow hole was excavated in the surface soil that would fit the soil in which the sentinel chambers and controls were placed. Two HOBO temperature data loggers were buried as close as possible to the sentinel chambers.

Microscopy.

All samples were examined using a Zeiss LSM-210 (1) in conventional DIC and epifluorescence mode using a triple excitation/emission filter set (Cat #61001, Chroma Technology Corp., Brattleboro Vt.) with excitation bands at 390–410, 485–510, and 555–585 nm and emission bands at 450–475, 510–550, and 595–660. A separate UV filter combination (excitation bands 310–395) was used for DAPI fluorescence. A Zeiss 100x/1.3 Plan-Neofluar DIC objective combined with 10x eyepieces was used for all microscopy procedures except for enumerations which were done with a Zeiss 40x/0.85 Plan-Neofluar DIC dry objective.

Statistical Analysis.

Except where otherwise stated, all statistical analyses of data were performed using Minitab Statistical Software (Miumnitab Inc., State College, Pa.).

Results

Sentinel Chamber Equilibration:

The ability of the 0.45 um nylon filter to allow the interior of the chamber to reach a state of chemical equilibrium with the exterior environment was indicated by the significant decrease from 98 to 9% viability of the oocysts in the chambers that were placed in ammonia for 24 hours compared to controls that remained at a level of viability >90%.

The built in 0.45 um nylon filter was also able to exchange exterior soil water and approach equilibrium with the bulk soil water content; the soil water content of the sentinel chamber would decrease parallel with the bulk soil water content as the bulk soil dried, and the interior soil water content would increase when the bulk soil was wetted (data not shown). Comparison of the bulk soil water content with the soil water content of the sentinel chambers with 60 um Spectramesh on the one end the chamber (so that exchange occurred at both ends) that were buried in the surface soil indicated that complete equilibrium between interior and exterior environments was obtained.

Temperature Experiment:

Over the five day duration of the experiment, the kinetics of inactivation significantly increased with each 5° C. increase above 30° C. (FIG. 1). At 30° C. there was no significant change over the 5 day period. Coefficients of inactivation are noted in Table 2.

Figure 2:
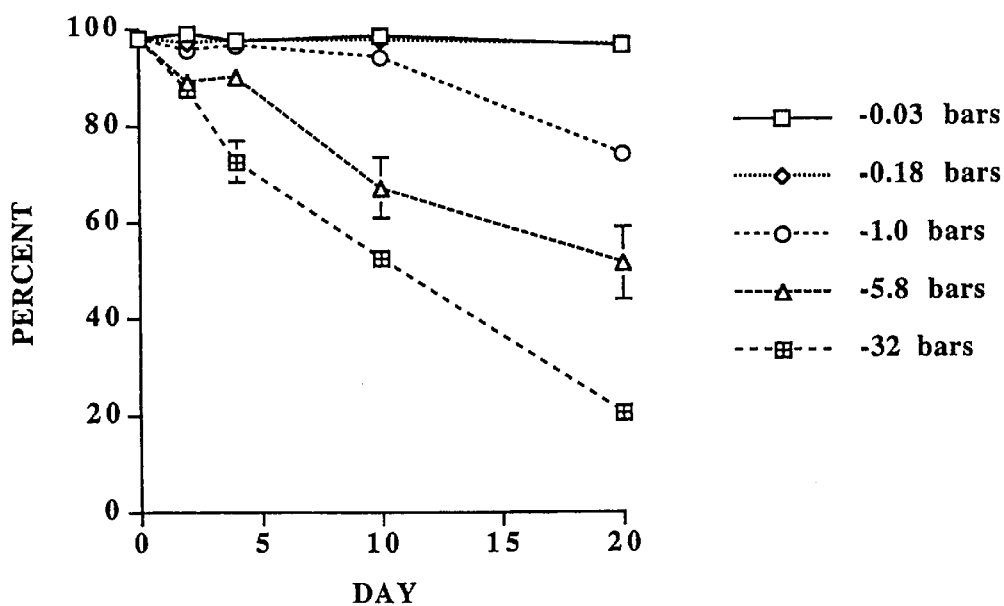

Soil Water Potential Experiment:

Although recovery of oocysts from the driest soil incubated at 4° C. was significantly lower than the wetter soil samples, and less than 100 oocysts were characterized per replicate, the frequency of potentially infective or viable oocysts observed were not significantly less than oocysts extracted from the wetter soil samples or the control oocysts (data not shown). It appeared that at 4° C., at least for a period of two days, that a soil water potential <−30 bars had little effect on oocyst survival. In contrast, at 25° C. significant decrease in oocyst viability occurred when the soil water potential was <4 bars, and rates of inactivation increased with further decrease in the soil water potential (FIG. 2). The water potentials nearest the water holding capacity of the soil (>−1.2 bars) negligibly affected the viability of the oocysts over the 20 day period of the experiment. At the most negative soil water potential 20% of the oocysts survived the 20 days of exposure, for a 1 log decrease in the potentially infective oocyst population. The distribution of dye-permeability categories of oocysts for the 20 day period of the experiment showed a slight increase in the semi-permeable DAPI+ PI− oocysts (approaching 20% at the 10 day sampling time-data not shown). Assuming that oocyst inactivation resulting from exposure to low soil water potentials is a first-order process, the coefficient of inactivation, K±95% confidence interval (Jenkins et al., 1997) were (day$^{-1}$) 0.014±0.003, 0.246±0.054, and 0.416±0.196 for oocysts exposed to soil water potentials of −1.0, −5.8, and −32 bars respectively.

Figure 3A:
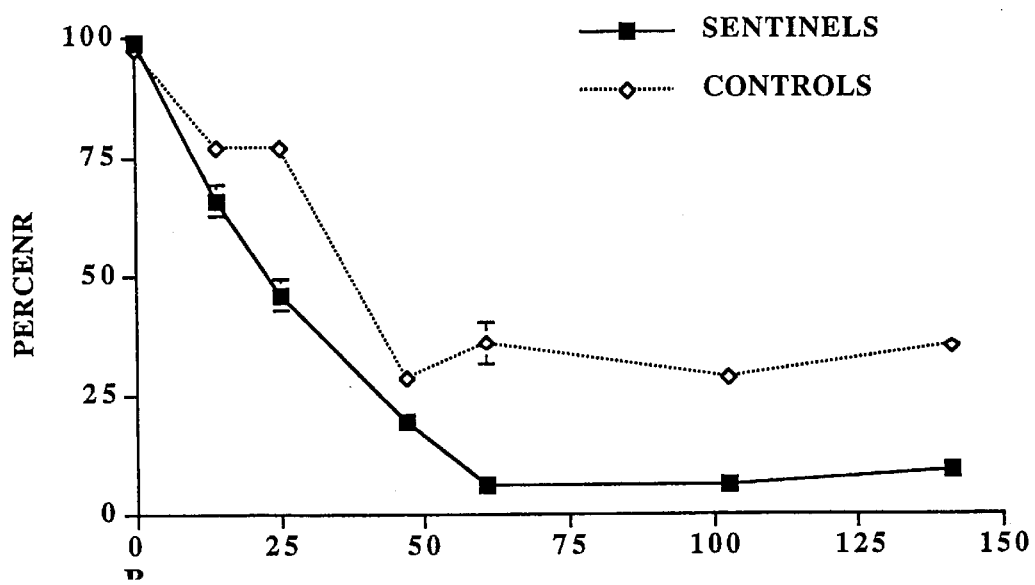
Figure 3B:
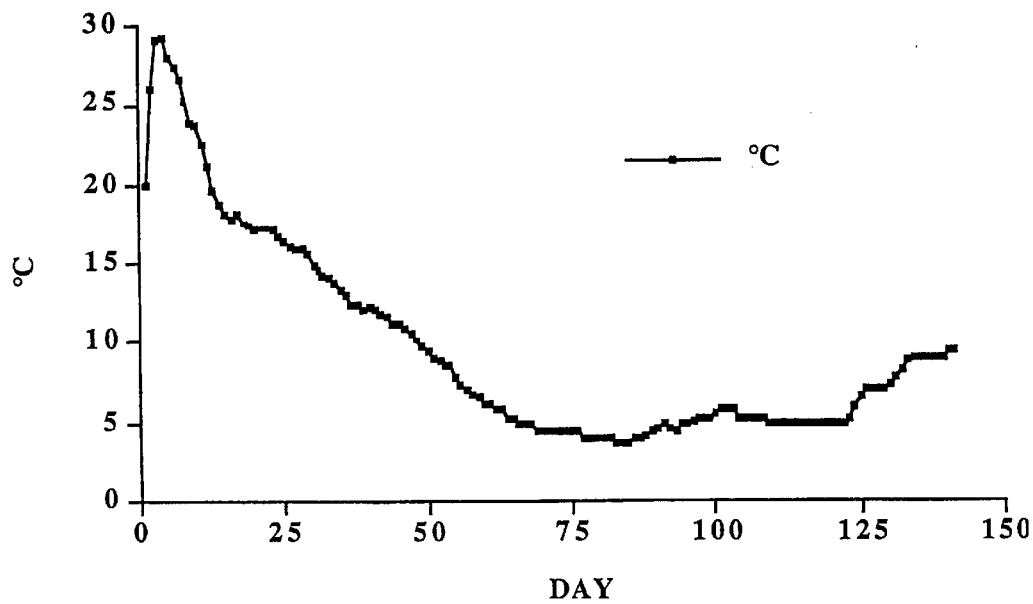
Figure 4A:
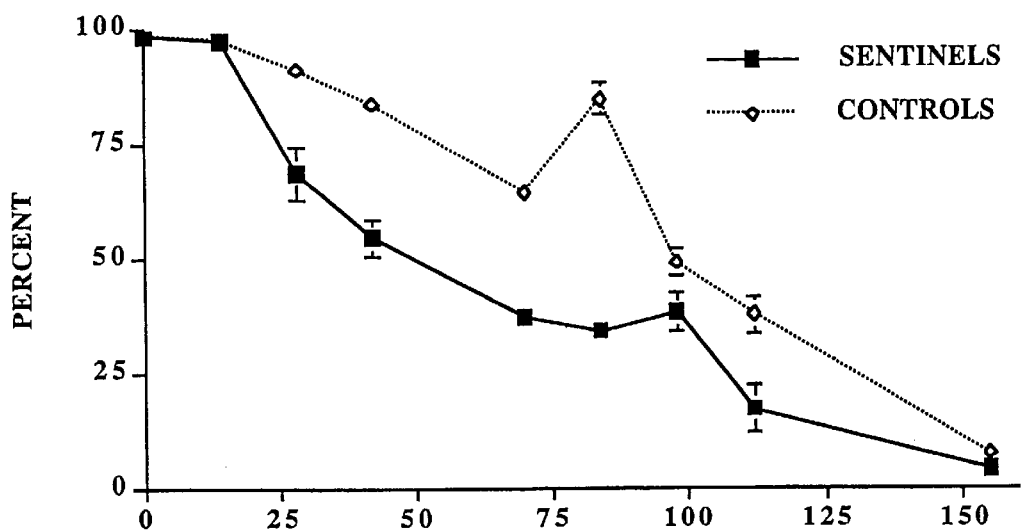
Figure 4B:
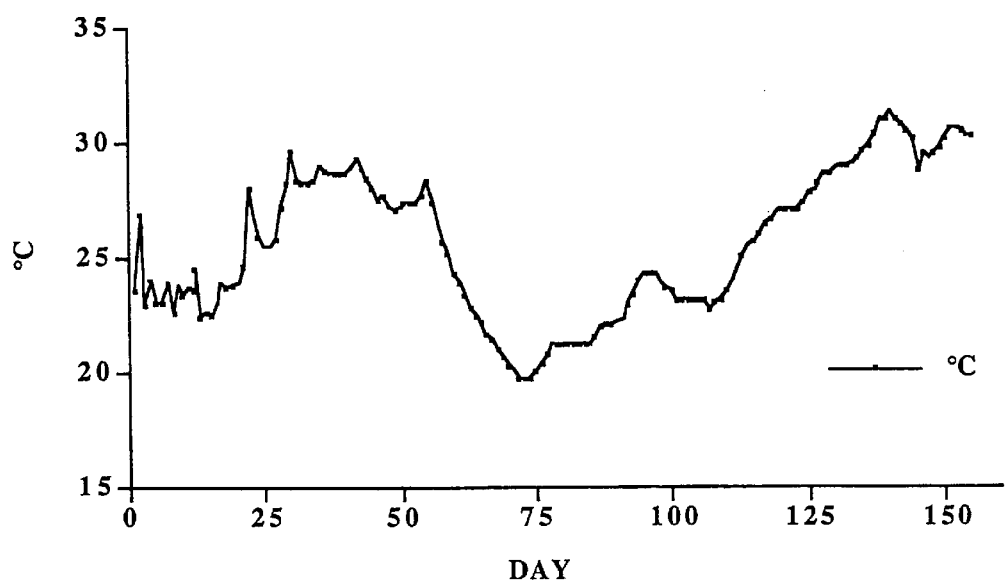

Sentinel Oocysts in a Passive Manure Pile:

The efficiency of oocyst extraction from the inoculated manure ranged from 52.8 to 90.5% and had a mean value±SD of 73.1±15.5%. The inactivation kinetics of the sentinel oocysts were for both manure piles significantly greater than the inactivation kinetics of the control oocysts (FIG. 3 and 4). The salient measurable difference between the two manure piles was their internal temperatures during the experiments. The first manure pile established in 1996–97 had an initial temperature at 30° C. at the time the sentinel oocysts were placed inside it; this temperature declined steadily to less than 10° C. as winter weather prevailed (FIG. 3). The manure pile established in 1998 (FIG. 4) maintained a higher internal temperature than the first pile. Its temperature fluctuated from approximately 27° C. to 23° C., then rose to above 30° C., fell to 20° C., then rose continuously to around 32° C. A low concentration of ammonia was generated from the breakdown of urea to $NH_3$ and $CO_2$ and other nitrogenous compounds. Although the phosphoric acid did not trap a detectable quantity of volatilized $NH_3$, analysis of the manure sample indicated that approximately 13 ppm $NH_3$ was present. The pH of the manure sample, at 9.1, further indicated a high probability that non-ionized $NH_3$ was present. The maintenance of a temperature greater than 30° C. may account for the accelerated inactivation rates of the control oocysts. Another principle difference between the two manure piles was indicated by the dye permeability assay. Results from the first manure pile indicated that for the sentinel oocysts actually exposed to the manure environment there was a significantly greater increase in DAPI+ PI+ and reciprocal decrease in DAPI− PI− oocysts compared to the controls (data not shown).

Figure 5A:
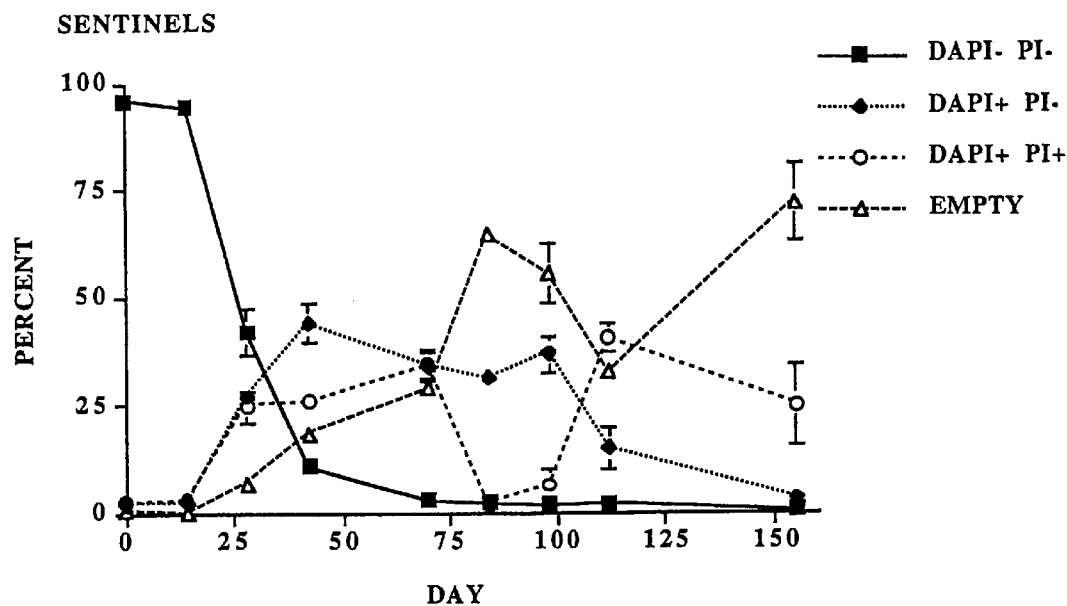
Figure 5B:
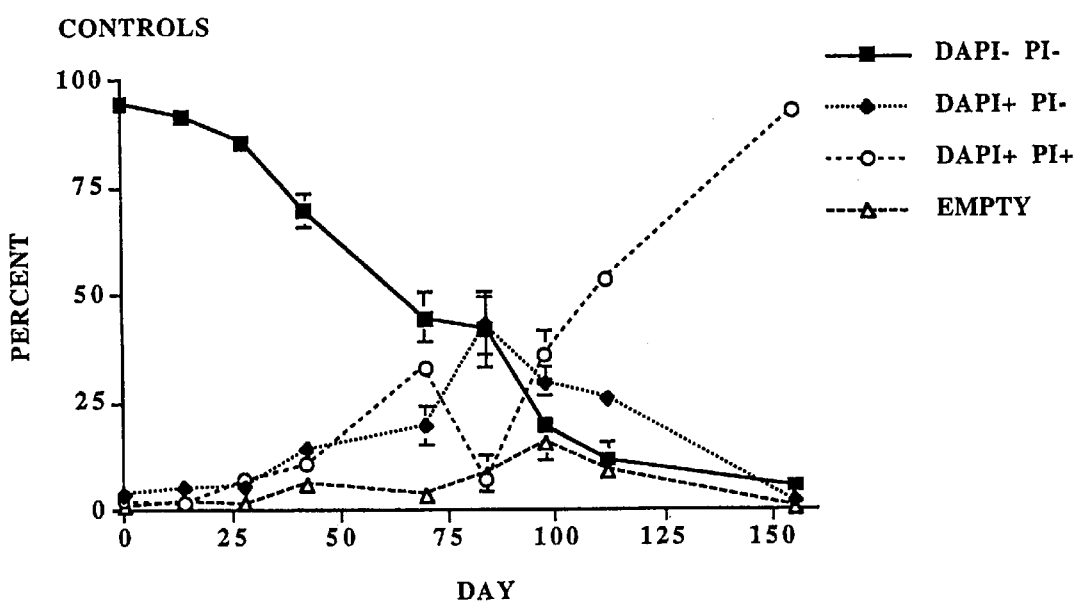

For the second manure pile results of the dye permeability assay (FIG. 5) indicated that for the sentinel oocysts there was a significant increase in the frequency of empty oocysts compared to the control oocysts that showed a pattern of dye categories similar to the controls of the first manure pile. The frequency of empty oocysts observed in the second manure pile were as high as 71%. These unexpected results suggest that the combination of elevated temperatures and possible surfactants or other unrecognized compounds in the liquid phase of the manure may have induced the oocysts to excyst, thus exposing the infectious sporozoites to a destructive environment.

Figure 6A:
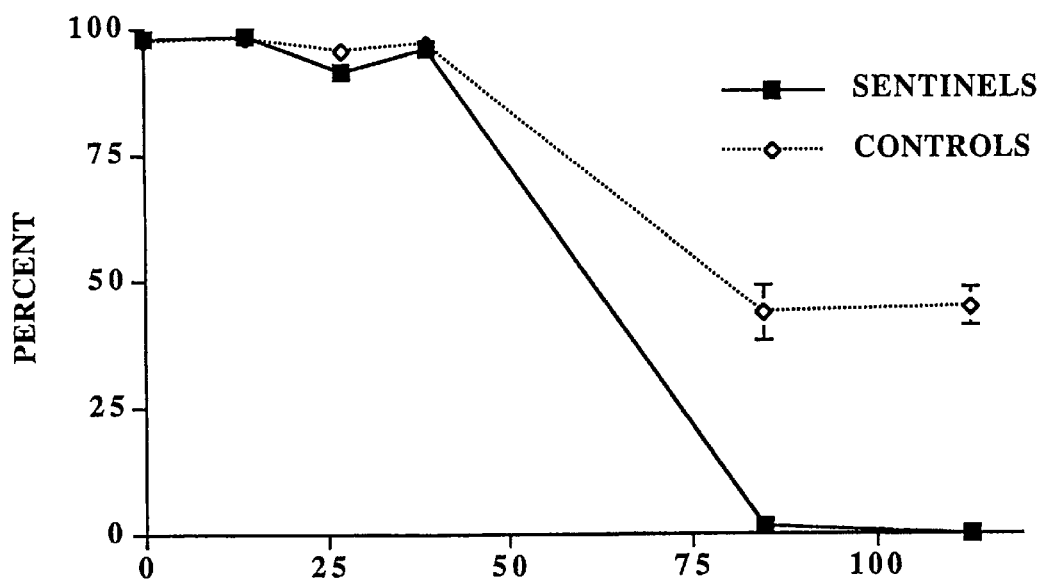
Figure 6B:
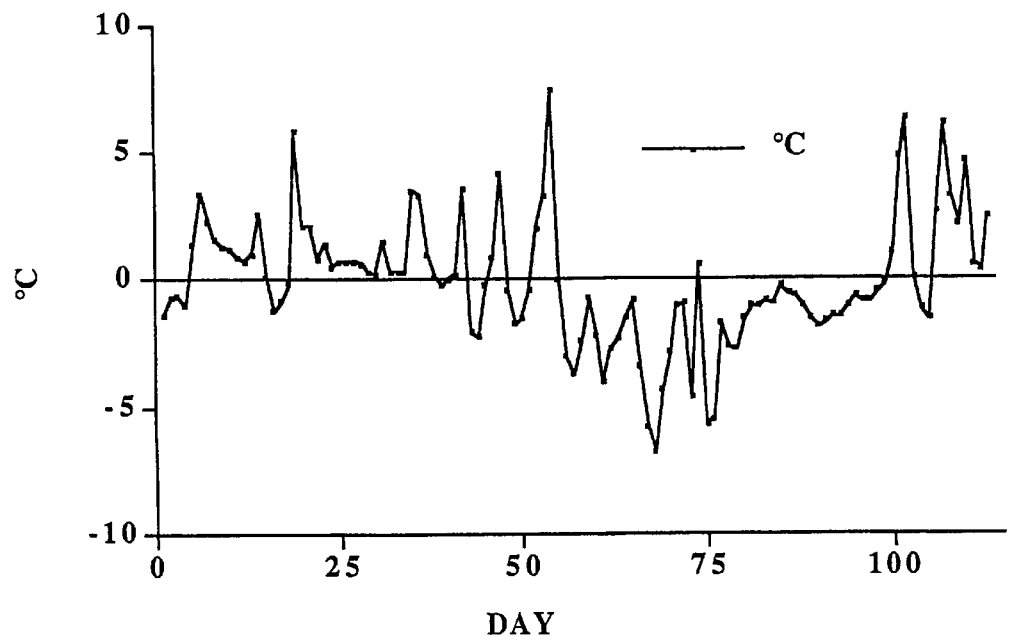
Figure 7A:
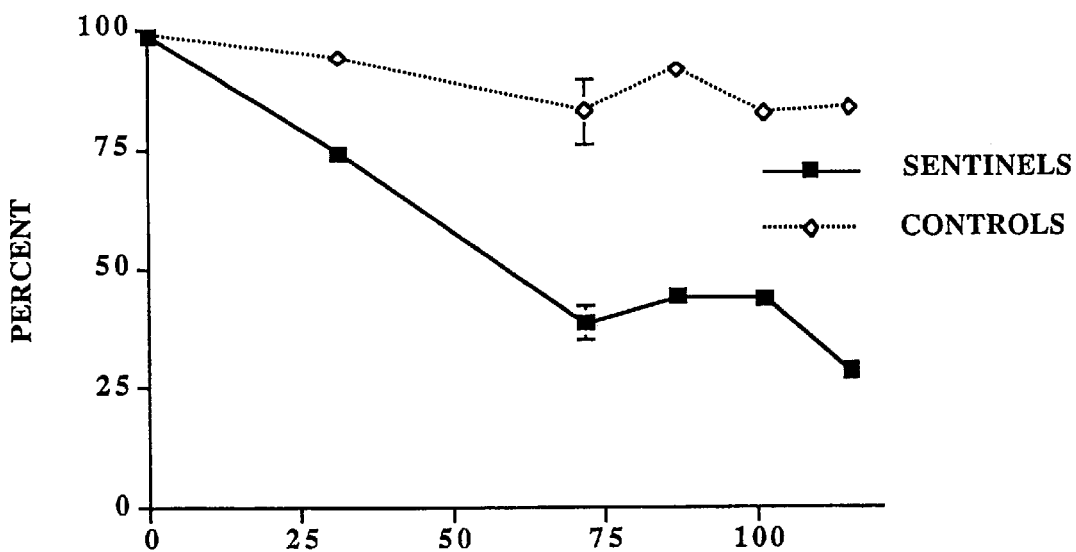
Figure 7B:
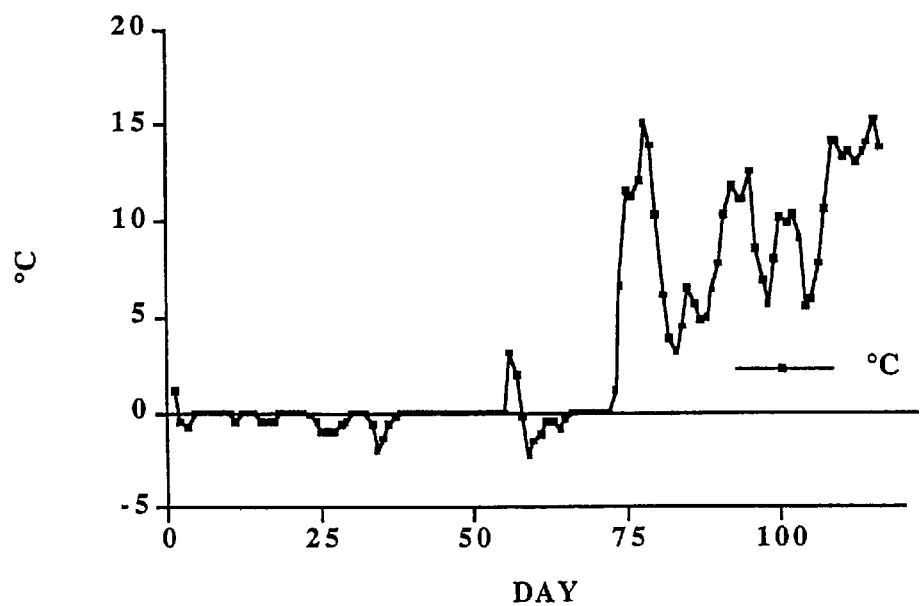

Sentinel Oocysts Exposed to Surface Soil in the Field:

Recovery efficiency of oocysts from the soil at −0.33 bars after 10 days of incubation at 24±1° C. was 90.0±2%. In contrast the extraction efficiency of oocysts from the soil in sentinel containers that had been exposed to the freeze-thaw cycles described below, and had soil water potentials ranging from −140 to <800 bars at time of extraction, ranged from 0.1 to 0.6% for a mean value±SD of 0.33±0.26%. Results of the first field experiment indicated that the inactivation kinetics of the sentinel oocysts significantly diverged from the control oocysts after a series of freeze-thaw events (FIG. 6). The day that the field experiment was established the soil was not frozen solid although the soil temperature was at −0.1° C.; brief fluctuations between −3.3 to 4. 1° C. occurred on the second day, and then remained subzero for days 3 and 4. The soil temperature then remained on the average between 0 and 4° C. to the 16th day when the soil temperature dropped to an average of −1.2° C., and hovered just below 0° C. until the 19th day when the soil temperature rose above freezing and remained between 1 and 3° C. until the 43rd day when the soil froze again and a series of freeze-thaw events occurred. Thawing occurred on days 45, 47, 52 to 55, 72, 74, 100 to 102, 103, 104, 106 to 107, 108, 110, and 113 for a sum of at least 13 freeze-thaw cycles. A similar divergence between sentinel oocysts and control oocysts was seen in the results of the second field experiment (FIG. 7).

The day after establishing the second field experiment, the soil temperature became subzero and remained subzero until days 56 and 57 when the first thaws occurred. Another thaw occurred on day 67, and the final thaw began on day 73. There appeared to be only three freeze-thaw cycles during the second field experiment. Between the establishment of the field site and the second sampling (which occurred when the soil temperature was −0.1° C., and partially frozen) the site was visited twice but recovering sentinel containers and controls was not possible because the soil was frozen solid; sampling was attempted and again failed between the second and third sampling days because the soil was frozen solid. The significantly fewer freeze-thaw cycles during the second field experiment probably accounts for the lesser extent and rate of inactivation for both sentinels and controls compared to the first field experiment.

Figure 8A:
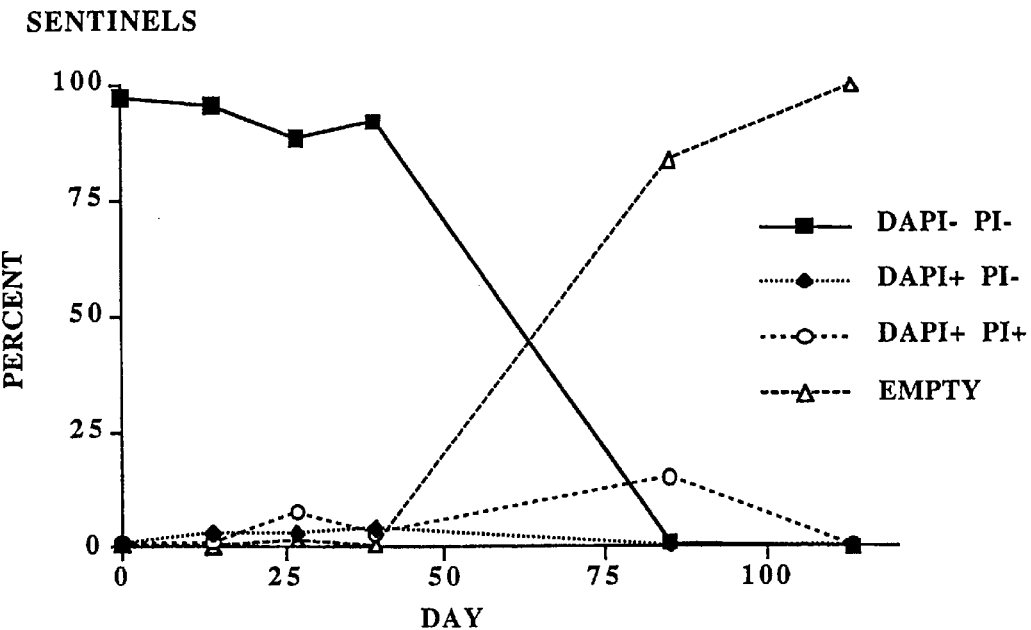
Figure 8B:
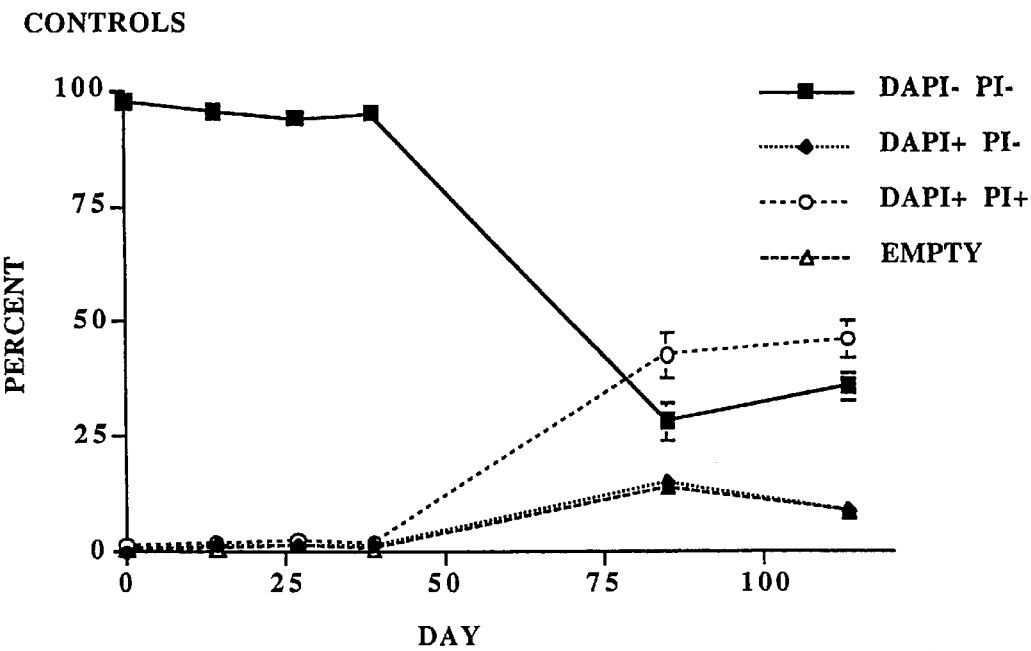
Figure 9A:
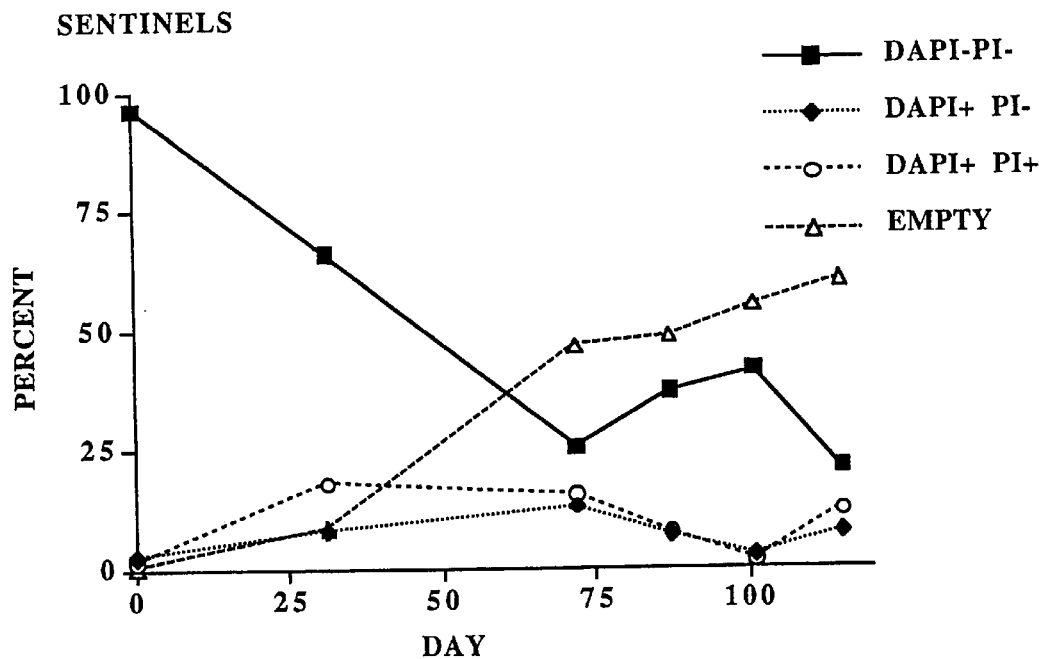
Figure 9B:
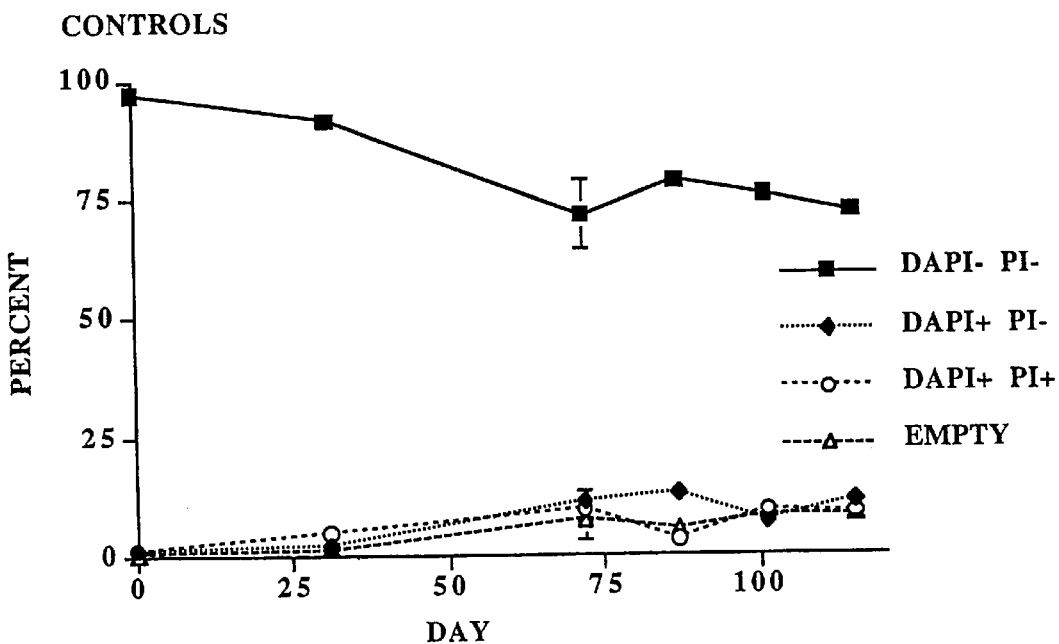
Figure 10:
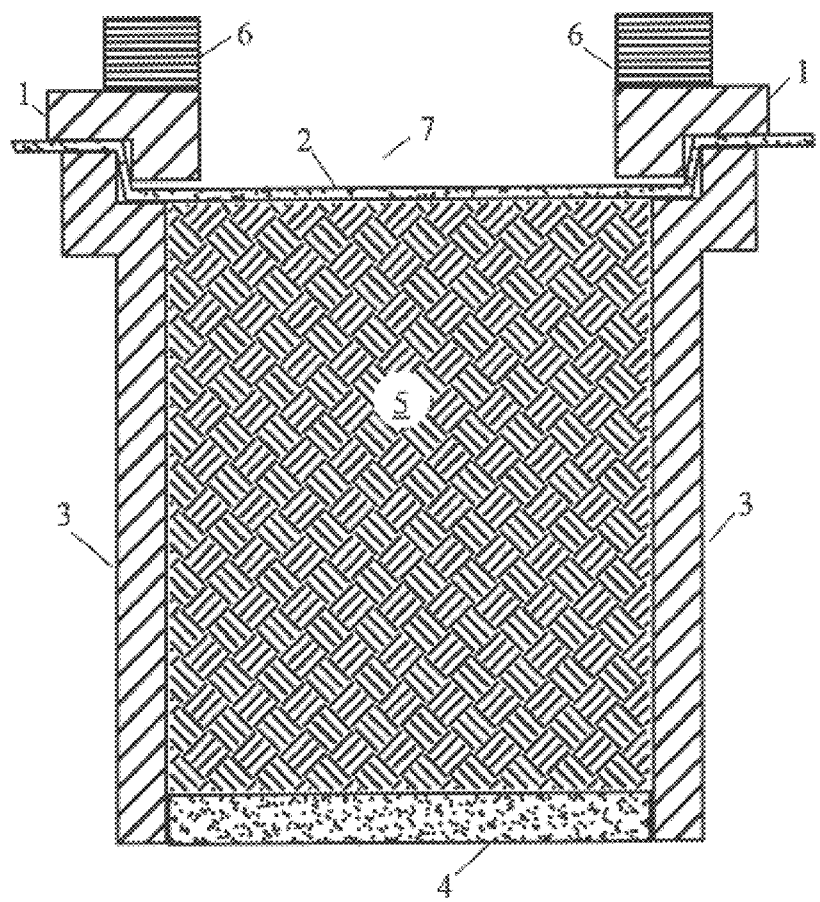

Results of the two field experiments indicated that freeze-thaw cycles in the presence of a solid matrix such as soil was more effective at inactivating oocysts than the freezing soil temperatures alone. Otherwise the control oocysts would have behaved in parallel. The most notable effect of the freeze-thaw cycles on the sentinel oocysts inoculated in the soil contained in the sentinel chambers was the significantly high frequency of empty oocyst shells compared to the control oocysts (FIGS. 8 and 9). The freeze-thaw cycles and associated expansion and contraction of water within the soil matrix appeared to disrupt oocyst walls.

Discussion

The environmental sentinel chambers used in our investigations proved effective at equilibrating with the external environment of both the manure piles and surface soil. In both environments, the differences in extent and rate of inactivation between sentinel oocysts and controls indicated the presence of factors other than temperature that affected oocyst survival. The variability in extraction efficiencies probably did not skew the results of the experiments. It appeared that the range of extraction efficiencies for the manure samples was not so great as to misrepresent the population of oocysts characterized. Likewise the water potentials of all the sentinel containers recovered from the field and extracted for oocyst viability determinations were either at 0 bars (saturated), or $\geq -0.33$ bars (near field capacity), thus decreasing the probability that the population of oocysts characterized was not truly representative. Qualitatively speaking, the number of oocysts observed per microscopic field for each extracted sample indicated an oocyst density $\geq 10^6$ sample$^{-1}$.

Although there were significant differences in the thermal behavior of the two manure piles, additional factors such as the probable microbial production of ammonia, and other metabolites must account for the significant increase in oocyst inactivation kinetics compared to control oocysts. It is well established that $NH_3$ volatilization is associated with stored animal wastes (Buijsman et al, 1987; Kirchmann and Witter, 1989; Dewes, 1996). The pH of the manure that surrounded the sentinels was basic enough at 9.1 for the presence of non-ionic $NH_3$ to be in equilibration with cationic $NH_4+$ in the liquid phase of the manure. Although volatilized $NH_3$ was not detected, low concentrations were extracted from the manure. Jenkins et at. (1998), demonstrated the deleterious effects of low environmental concentrations of ammonia on oocysts especially at temperatures >20° C. The results of the temperature experiments (FIG. 1) suggest that if manure piles can be manipulated to reach and maintain temperatures between 35 and 50° C. that significant declines in potential oocyst infectivity may result over a period between 3 to 70 days. The significantly high frequency of empty, (excysted) oocysts observed during the second manure pile experiment indicated that factors other than acidity (Campbell et al., 1992), and temperatures around 37° C. (Fayer and Leek, 1984) may have been present in the manure environment. For example, microbially produced surfactants or other compounds may have been present that were capable of inducing the suture of the oocysts to open and expose the sporozoites to a lethal environment.

Inactivation of the sentinels exposed to the soil environment was significantly greater than the control oocysts for both the first and second field experiments indicating the significance of exposure to the soil matrix as a factor accelerating oocyst inactivation.

The principal difference between the first and second field experiments was the greater frequency of freeze-thaw cycles for the winter of 1997 than for the winter of 1998. Although the El Niño winter of 1998 was milder than the winter of 1997 when soil temperatures dipped below 5° C., the difference in temperature was probably not significant in affecting oocyst inactivation in light of a survival study reported by Fayer and Nerad (1996). Using mouse infectivity, they showed that oocysts exposed to temperatures as low as −10° C. for as long as 7 days remained infective. In fact, they predicted that surface soil temperatures just below freezing and insulated by a cover of snow (as was the case for both of the field trials) could sustain the survival of oocysts for weeks or months.

The survival of the control oocysts during the first 50 days, as well as the survival of the sentinel oocysts during the first four weeks of the second field trial appears to validate their prediction. As our laboratory results indicated, oocysts in soil at a water potential of −1.2 bars (a state somewhat drier than soil at its water holding capacity) at 25° C. can survive for many days. Oocysts in soil at temperatures between 0 and 5° C. can survive soil water potentials significantly more negative than −1.2 bars. The soil water potentials at the field site during the time of the experiment was either 0 bars (saturated), or around −0.2 bars (which is around field or water holding capacity). Therefore, soil water potential was not a significant factor in the inactivation of sentinel oocysts exposed to the soil environment.

Our results indicated that removing manure and bedding that contained *C. parvum* oocyst from calf housing facilities, and placing the material into a pile can accelerate the inactivation of the oocysts, and thus reduce the numbers of infective oocysts before spreading over a field. Thus passively piling calf manure before spreading it on a field may be used as a management practice for reducing the oocyst load from dairy farms located in municipal watersheds. Furthermore, by incorporating manure and oocysts into the soil before the soil freezes has the potential of inactivating 99.99% of the oocysts. Spreading oocysts on snow, as the controls in our field soil experiments indicated, can in effect sustain the survival of oocysts, and put them in a position to be transported with surface runoff.

METHOD EXAMPLE 2

Use of Sentinel *Cryptosporidium parvum* Oocysts to Measure Effects of Passive Manure Storage on Oocyst Inactivation Recently purified oocysts of *Cryptosporidium parvum* were used as sentinels to measure the effect of the passive composting of neonatal calf manure and bedding on oocyst inactivation. The basket of a microfiltration system with a 0.45 um nylon filter were filled with dried, sieved, oocyst-free manure. The dried manure was brought to near saturation with sterile distilled water and then inoculated with $2 \times 10^6$ freshly purified oocysts. A hole was cut in the cap of the basket, and was used to secure a piece of 60 $\mu$m nylon mesh filter material.

This sentinel system had been tested to demonstrate its ability to equilibrate with exogenous solutes gases, and water potential, and to retain inoculated oocysts. To facilitate removal of the sentinels from the manure pile as it increased In height, triplicate sentinels and controls (consisting of $2 \times 10^6$ oocysts in 1 ml of sterile PBS in 1.5-ml microfuge tubes) were secured to fishing line and placed at the end of 2.5-m long, 60-mm diameter plastic pipe. The ends of the pipe were cut in half to form a trough into which the sentinels and controls were placed and allowing them to be completely exposed to the manure.

Two data loggers for recording ambient manure temperature every 6 h for the duration of the experiment were placed next to the sentinels and controls. Oocyst viability was determined using a dye-permeability assay (Anguish & Ghione 1997, *Applied Environmental Microbiology* 63. 724–733), Sentinels and controls were removed from the manure pile on days 14, 25, 47, 61, 103 and 145. Oocysts wore extracted from the contents of the sentinels by sucrose flotation. A haemocyclometer was used to quantify extracted oocysts. The ambient temperature of the manure rose from an initial 10° C. to 29° C. in the first five days of the experiment, fell to 15° C. after 30 days, was at its lowest, 4° C., after 80 days and then steadily increased until the study's termination.

Inactivation of oocysts was significantly greater for the sentinels than the controls. On days 14 and 25, viability of sentinel oocysts was significantly less than controls. From day 47 to the termination of die study, 30% of the control oocysts were consistently viable. The percentage of viable sentinel oocysts continually declined throughout the study with <10% remaining viable after 103 days. These data indicate that storing calf manure in piles can decrease the viability of *C. parvum* oocysts by >90% in the late fall and early winter (November through February). Thus, storing *C. parvum* infected calf manure during the winter months before spreading it on fields could significantly reduce the risk of contaminating surface waters during spring run-off events.

REFERENCES

Anguish, L. J. and W. C. Ghiorse. 1997. Computer-assisted laser scanning and video microscopy for analysis of *Cryptosporidium parvum* oocysts in soil, sediment, and feces. Appl. Environ. Microbiol. 63:724–733.

Blewett, D. A. 1989. Quantitative techniques in Cryptosporidium research, p. 85–95. In: Angus, K. W. and D. A. Blewett (eds.), Cryptosporidiosis. Proceedings of the First International Workshop. The Animal Diseases Research Association, Edinburgh, UK.

Buijsman, E., H. F. M. Maas, and W. A. H. Aasman. 1987. Anthropogenic $NH_3$ emissions in Europe. Atmospheric Environ. 21:1009–1022.

Campbell, A. T., L. J. Robertson, and H. V. Smith. 1992. Viability of *Cryptosporidium parvum* oocysts: correlation in vitro excystation with inclusion or exclusion of fluorogenic vital dyes. Appl. Environ. Microbiol. 58:3488–3493.

Current, W. L. and L. S. Garcia. 1991. Cryptosporidiosis. Clin. Microbiol. Rev. 4:325–258.

Dewes, T. 1996. Effect of pH, temperature, amount of litter and storage density of ammonia emissions from stable manure. J. Agric. Res. 127:501–509.

Fayer, R. 1994. Effect of high temperature on infectivity of *Cryptosporidium parvum* oocysts in water. Appl. Environ. Microbiol. 60:2732–2735.

Fayer, R. and R. G. Leek. 1984. The effects of reducing conditions, medium, pH, temperature, and time on in vitro excystation of Cryptosporidium. J. Protozool. 31:567–569.

Fayer, R. and T. Nerad. 1996. Effect of low temperatures on viability of *Cryptosporidium parvum* oocyst. Appl. Environ. Microbiol. 62:1431–1433.

Hillel, D. 1971. Soil and water. Academic Press, New York, N.Y. pp. 288.

Jenkins, M. B., L. J. Anguish, D. D. Bowman, M. J. Walker, and W. C. Ghiorse. 1997. Assessment of a dye permeability assay for determination of inactivation rates of *Cryptosporidium parvum* oocysts. Appl. Environ. Microbiol. 63:3844–3850.

Jenkins, M. B., D. D. Bowman, and W. C. Ghiorse. 1998. Inactivation of *Cryptosporidium parvum* oocysts by ammonia. Appl. Environ. Microbiol. 64:784–788.

Kirchmann, H., and E. Witter. 1989. Ammonia volatilization during aerobic and anaerobic manure decomposition. Plant Soil. 115:35–41.

MacKenzie, W. R., N. J. Hoxie, M. E. Proctor, S. Gradus, K. A. Blair, D. E. Peterson, J T Kazmierczak, K. Fox, D. G. Addis, J. B. Rose, and J T Davis. 1994. Massive waterborne outbreak of Cryptosporidium infection associated with a filtered public water supply, Milwaukee, March and April, 1993. New England J. Med. 331:161–167.

Madore, M. S., J. B. Rose, C. P. Gerba, M. J. Arrowood, and C. R. Sterling. 1987. Occurrence of Cryptosporidium oocysts in sewage effluents and selected surface waters. J. Parasitol. 73:702–705.

Moore, A. C., B. L. Herwaldt, G. F. Craun, R. L. Calderon, A. K. Highsmith, and D. D. Juranek. 1994. Waterborne disease in the United States, 1991–1992. J. Am. Water Works Assoc. 86(2):87–99.

Pavelic, P., et. al., Diffusion Chamber Method For In Situ Measurement Of Pathogen Inactivation In Groundwater, Water Resources 32(4), pg. 1144 (1998).

Peng, M. M., L. Xiao, A. R. Freeman, M T Arrowood, A. A. Escalante, A. C. Weltman, C. S. L. Ong, W. R. MacKenzie, A. A. Lal, and C. B. Beard. Genetic polymorphisms among *Cryptosporidium parvum* isolates: evidence of two distinct human transmission cycles. Emerging Infectious Diseases 3:567–573.

Roberson L. J., A. T. Campbell, and H. V. Smith. 1992. Survival of *Cryptosporidium parvum* oocysts under various environmental pressures. Appl. Environ. Microbiol. 58:3494–3500.

Roberson, L. J., A. T. Campbell, and F I N. Smith. 1993. A low cost, low technology container for studying the survival of transmission stages of parasites and other pathogens in water-related environments. Wat. Res. 27:723–725.

Rose, J. B. 1988. Occurrence and significance of Cryptosporidium in water. J. Am. Water Works Assoc. 80:53–58.

Rose, J. B., A. Cifrino, M. S. Madore, C. P. Gerba, C. R. Sterling, and M. J. Arrowood. 1986. Detection of Cryptosporidium from wastewater and freshwater environments. Water Sci. Technol. 18:233–239.

Topp, G. C. 1971. Soil water hysteresis in silt loam and clay loam soils. Wat. Resources Res. 7:914–920.

Walker, M. J., C. Montemagno, J. C. Bryant, and W. C. Ghiorse. 1998. Method detection limits of PCR and immunofluorescence assay for *Cryptosporidium parvum* in soil. Appl. Environ. Microbiol. 64:2281–2283.

Weatherburn, M. W. 1967. Phenol-hypochlorite reaction for determination of ammonia. Anal. Chem. 39:971–974.

What is claimed is:

1. A sentinel chamber for containing microorganisms in a matrix in communication with an external environment, comprising:

a) a body enclosing an interior volume;

b) a matrix for containing microorganisms inside the interior volume;

c) at least one area of the body comprising a filter material having a plurality of openings small enough that gases or liquids may pass through the filter material into the interior volume from the external environment, but the matrix in the interior volume is prevented from leaving; wherein the matrix inside the interior volume is related to the external environment where the sentinel chamber is to be placed.

2. The sentinel chamber of claim 1, wherein the matrix is selected from the group consisting of:

a) soil;

b) manure;

c) sand; and d) sewage sludge.

3. The sentinel chamber of claim 1, further comprising a sentinel microorganism in the matrix in the interior volume.

4. The sentinel chamber of claim 3, in which the sentinel organism is a *Cryptosporidium parvum* oocyst.

5. The sentinel chamber of claim 3, in which the sentinel organism is *Ascaris suum* eggs.

6. The sentinel chamber of claim 3, in which the sentinel organism is *Giardia lamblia* cysts.

7. The sentinel chamber of claim 3, wherein the sentinel organism is capable of fluorescing.

8. The sentinel chamber of claim 5, wherein a fluorescent stain is incorporated into the sentinel organism.

9. The sentinel chamber of claim 5, wherein a gene for a fluorescent protein is incorporated into the sentinel organism.

10. The sentinel chamber of claim 1, wherein the filter material is a mesh filter.

11. The sentinel chamber of claim 1, wherein the filter material is a sintered metal filter.

12. The sentinel chamber of claim 1, wherein the sentinel chamber is pre-loaded with a sentinel organism in a liquid medium.

13. The sentinel chamber of claim 12, further comprising particulate matter mixed into the liquid medium.

14. The sentinel chamber of claim 1, further comprising a magnetic metal in association with the body, such that the sentinel chamber can be recovered by a magnet or a metal detector.

15. The sentinel chamber of claim 14, in which the sentinel chamber has a buoyancy and the size of the magnetic metal is selected to at least partially counteract the buoyancy of the sentinel chamber.

16. The sentinel chamber of claim 14, in which the body has at least one removable cap and the magnetic metal is in the form of a ring forming at least part of the cap.

17. The sentinel chamber of claim 1, further comprising at least one removable cap having an opening therethrough, the cap being selected to fit over an opening in the body.

18. The sentinel chamber of claim 17, in which the filter material is attached to the removable cap, covering the opening.

19. A method of using a plurality of sentinel chambers to study at least one characteristic of a sentinel organism in a particular environment, comprising the steps of:

a) selecting a sentinel chamber comprising:

i) a body enclosing an interior volume;

ii) at least one part of the body comprising a filter material having a plurality of openings small enough that gases or liquids may pass through the filter material into the interior volume from the external environment, but a matrix in the interior volume is prevented from leaving;

b) filling the sentinel chamber with a matrix related to the external environment where the sentinel chamber is to be placed;

c) introducing a sentinel organism into the matrix;

d) repeating steps (a) through (c) until a sufficient quantity of the sentinel chambers are prepared;

e) placing the plurality of sentinel chambers in situ in an external environment which corresponds to the matrix inside the sentinel chambers.

20. The method of claim 19, further comprising the steps, after step (e), of:

i) recovering at least one of the sentinel chambers; and j) analyzing the sentinel organism in the sentinel chamber.

21. The method of claim 20, further comprising repeating steps (i) and (j) at different time points in order to ascertain the at least one characteristic of the plurality of sentinel organisms in the environment over a period of time.

22. The method of claim 19, wherein the matrix is selected from the group consisting of:

a) soil;

b) manure;

c) sand; and d) sewage sludge.

23. The method of claim 19, in which the sentinel organism is a *C. parvum* oocyst.

24. The method of claim 19, in which the sentinel organism is *Ascaris suum* eggs.

25. The method of claim 19, in which the sentinel organism is *Giardia lamblia* cysts.

26. The method of claim 19 wherein the sentinel organism is capable of fluorescing.

27. The method of claim 26, wherein a fluorescent stain is incorporated into the sentinel organism.

28. The method of claim 26, wherein a gene for a fluorescent protein is incorporated into the sentinel organism.

29. The method of claim 19, wherein the filter material is a mesh filter.

30. The method of claim 19, wherein the filter material is a sintered metal filter.

31. The method of claim 19, in which the sentinel chamber further comprises a magnetic metal in association with the body, such that the sentinel chamber can be recovered by a magnet or a metal detector.

32. The method of claim 19, wherein at least one piece of monitoring equipment is buried with or around the sentinel chambers in order to take at least one measurement of the environment.

33. The method of claim 19, further comprising the step, before step (b) of sterilizing the matrix.

34. The method of claim 19, further comprising the step of hydrating the matrix by the addition of distilled water.

* * * * *